(12) United States Patent
Le et al.

(10) Patent No.: US 8,516,877 B2
(45) Date of Patent: Aug. 27, 2013

(54) DROP TEST APPARATUS

(75) Inventors: Yin Le, Shenzhen (CN); Yu-Lin Liu, Shenzhen (CN); Qiang Zhang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 319 days.

(21) Appl. No.: 12/964,265

(22) Filed: Dec. 9, 2010

(65) Prior Publication Data

US 2012/0017664 A1 Jan. 26, 2012

(30) Foreign Application Priority Data

Jul. 23, 2010 (CN) .......................... 2010 1 0234747

(51) Int. Cl.
*G01N 3/00* (2006.01)
*G01N 19/02* (2006.01)

(52) U.S. Cl.
USPC ........................... 73/12.06; 248/127; 248/371

(58) Field of Classification Search
USPC .................. 73/12.04, 12.01, 12.06; 248/127, 248/371, 393, 394, 396, 346.01, 346.03, 248/346.06, 346.5
See application file for complete search history.

(56) References Cited

U.S. PATENT DOCUMENTS

| | | | | |
|---|---|---|---|---|
| 2,634,542 A | * | 4/1953 | Bode | 248/457 |
| 2,822,687 A | * | 2/1958 | Freedy | 73/12.06 |
| 3,224,249 A | * | 12/1965 | Ford et al. | 73/12.06 |
| 3,310,273 A | * | 3/1967 | Seymour | 248/346.03 |
| 3,739,406 A | * | 6/1973 | Koetter | 5/608 |
| 6,807,841 B1 | * | 10/2004 | Chen et al. | 73/12.06 |
| 7,913,539 B2 | * | 3/2011 | Su | 73/12.06 |

\* cited by examiner

*Primary Examiner* — Harshad R Patel
*Assistant Examiner* — Roger Hernandez-Prewitt
(74) *Attorney, Agent, or Firm* — Altis Law Group, Inc.

(57) ABSTRACT

A drop test apparatus includes a base panel, at least one height adjustment member attached to the base panel, and at least one angle adjustment member pivotally attached to the at least one height adjustment member. The at least one height adjustment member has a portion protruding upward from the base panel. A height of the portion is variable. The at least one angle adjustment member is configured for supporting a device thereon and capable of rotating to different angles.

16 Claims, 3 Drawing Sheets

DROP TEST APPARATUS

TECHNICAL FIELD

The present disclosure relates to device testing, and more particularly to a drop test apparatus.

DESCRIPTION OF RELATED ART

In drop testing, a container filled with varying contents is dropped from a preset height onto a rigid surface to determine whether the container and its contents can resist the impact. A typical drop test apparatus employed for this purpose includes a support platform and a control device for adjusting a height of the support platform. After the container reaches the predetermined height, the control device withdraws the support platform and the container falls. The container and its contents are checked fro damage. Such a drop test apparatus controls the height from which the container drops, but cannot control the angle at which the container falls.

Therefore, there is room for improvement within this art.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation. In the figures of the accompanying drawings in which like references indicate similar elements. It should be noted that references to "an" or "one" embodiment in this disclosure are not necessarily to the same embodiment, and such references mean at least one.

Figure 1:
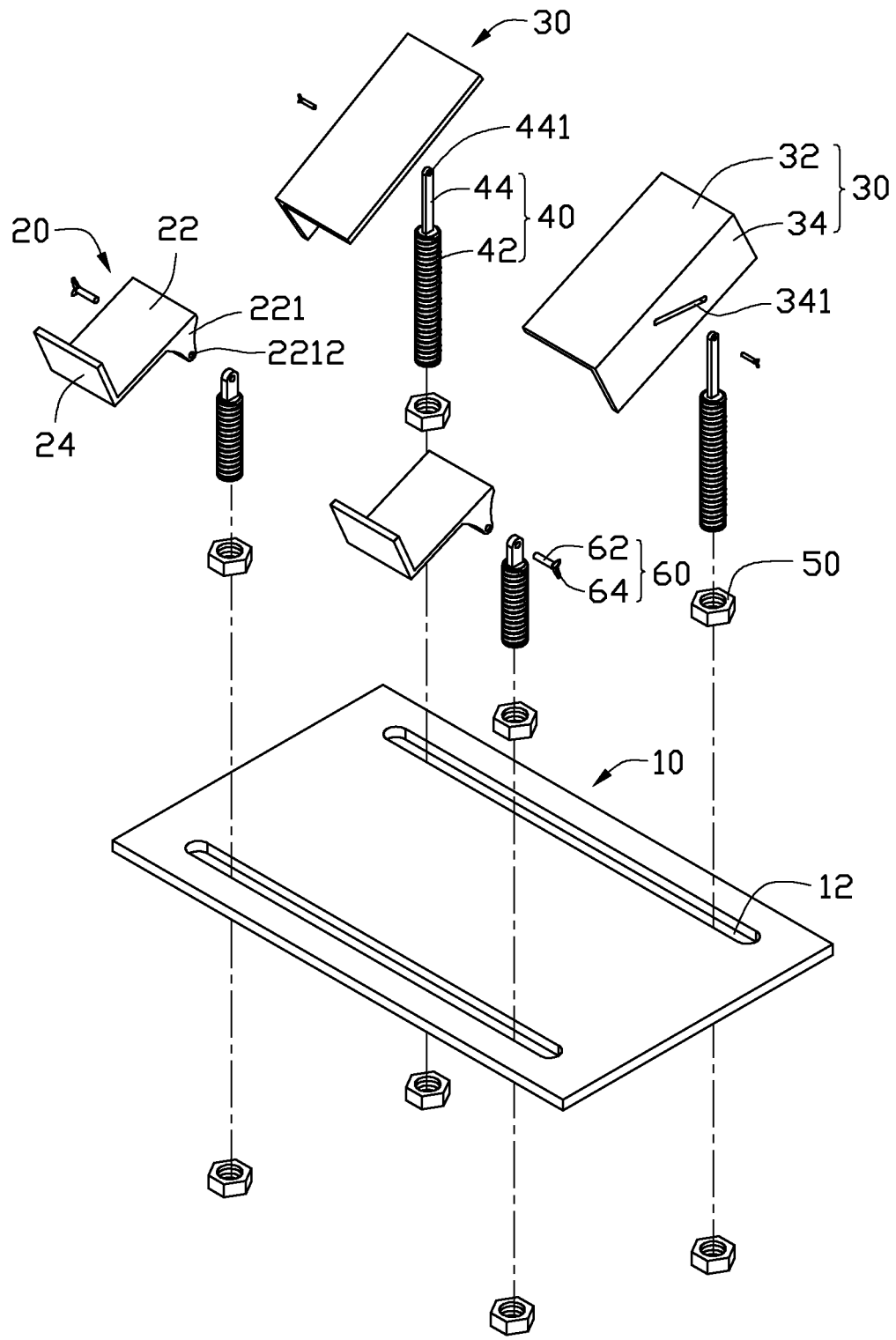
FIG. 1 is an isometric and exploded view of a drop test apparatus in accordance with an embodiment.

Referring to FIG. 1, an embodiment of a drop test apparatus includes a base panel 10, a pair of first angle adjustment members 20, a pair of second angle adjustment members 30, two pairs of height adjustment members 40, four pairs of threaded retainers 50, and four pivot mounting members 60. A pair of longitudinal slots 12 is defined in the base panel 10 for mounting the height adjustment members 40. The longitudinal slots 12 are parallel.

Each of the first angle adjustment members 20 includes a first support panel 22, a backrest panel 24 extending upward from the first support panel 22, and a wedge-shaped mounting block 221 extending from a bottom side of the first support panel 22. The backrest panel 24 and the mounting block 221 are at opposite ends of the first support panel 22. A pivot mounting slot 2212 is defined in the mounting block 221 for receiving the pivot mounting member 60.

Each of the second angle adjustment members 30 includes a second support panel 32 and a side panel 34 extending downwardly from a side edge of the second support panel 32. Each of the second support panel 32 and the side panel 34 has a rectangular shape. An angled slot is defined in the side panel 34.

Each of the height adjustment members 40 includes a threaded post 42 and a mounting piece 44 protruding from a top thereof. A pivot hole 441 is defined in a top portion of the mounting piece 44.

Each of the pivot mounting members 60 includes a pivot shaft 62 and a V-shaped head 64 connected to a distal end of the pivot shaft 62.

Figure 2:
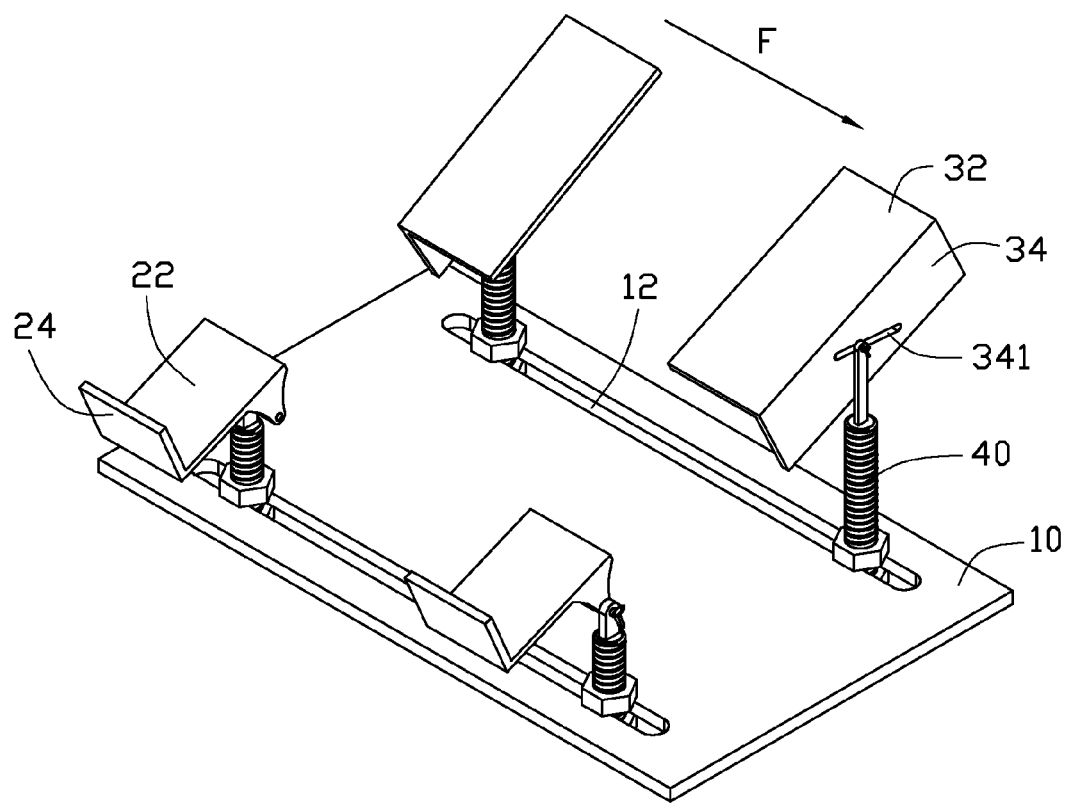
FIG. 2 is an assembled view of FIG. 1.
Figure 3:
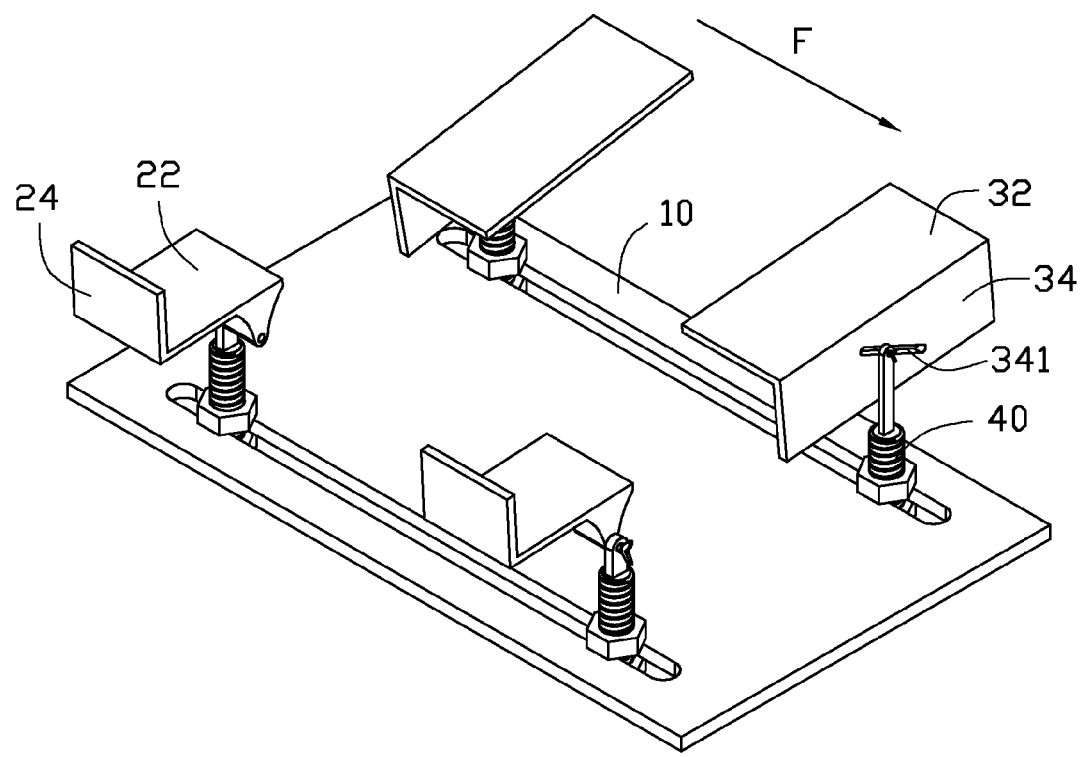
FIG. 3 is similar to FIG. 2, but shows angle adjustment members of the drop test apparatus at another height and angle.

Referring to FIGS. 2 and 3, during assembly, the threaded post 42 of each of the height adjustment members 40 is received in one of the longitudinal slots 12 of the base panel 10. A lower portion of the threaded post 42 of each of the height adjustment members 40 extends from a lower side of the base panel 10 via the longitudinal slot 12. A pair of threaded retainers 50 is secured to the threaded post 42 of each of the height adjustment members 40. The pair of threaded retainers 50 secured to each of the height adjustment members 40 respectively resist upper and lower surfaces of the base panel 10. Thus, each of the height adjustment members 40 can be secured to the base panel 10, and has a portion with a predetermined height protruding upwardly from the base panel 10. The pivot holes 441, of two of the height adjustment members 40, are aligned with the pivot mounting slots 2212 of the first angle adjustment members 20. Two of the pivot mounting members 60 are inserted into the pivot holes 441 and the pivot mounting slots 2212, for pivotally mounting the first angle adjustment members 20 to the height adjustment members 40. The pivot holes 441 of two of the height adjustment members 40 align with predetermined portions of the angled slots 341 of the second angle adjustment members 30. Two of the pivot mounting members 60 are inserted into the pivot holes 441 and the angled slots 341 for pivotally mounting the second angle adjustment members 30 to the height adjustment members 40.

To perform a drop test on a device (e.g., a cuboid casing with an electronic device packaged therein), the first angle adjustment members 20 and the second angle adjustment members 30 are rotated until reaching a predetermined angle and fixed at the predetermined angle by static friction. At the predetermined angle, the support panels 22 of the first angle adjustment members 20 and the support panels 32 of the second angle adjustment members 30 locate at a same plane. The device is placed on first angle adjustment members 20 and the second angle adjustment members 30. The backrest panels 24 of the first angle adjustment members 20 resist and maintain the position of the device until the drop test begins. The drop test apparatus is quickly withdrawn in a horizontal direction F (see FIGS. 2 and 3) by a control machine. The device loses support and falls to a rigid surface below. Faces, edges, and corners of the device are checked for damage by the impact.

In one embodiment, a height of each of the height adjustment members 40 is adjustable by a manner of adjusting a length of the each of height adjustment members 40 or adjusting a vertical position of each of the height adjustment members 40. Furthermore, the pivot mounting members 60 can be received in the angled slots 341 of the second angle adjustment members 30 in different positions, which can also change the height of the second angle adjustment members 30. Thus, the device can fall from various heights. The first angle adjustment members 20 and the second angle adjustment members 30 can rotate to different angles to support the device. Thus, the device can be dropped from various angles.

The drop test apparatus of the present disclosure can perform various drop tests on the device. The less it improves test accuracy and reliability.

While the present disclosure has been illustrated by the description of preferred embodiments thereof, and while the preferred embodiments have been described in considerable detail, it is not intended to restrict or in any way limit the scope of the appended claims to such details. Additional advantages and modifications within the spirit and scope of the present invention will readily appear to those skilled in the art. Therefore, the present disclosure is not limited to the specific details and illustrative examples shown and described.

What is claimed is:

1. A drop test apparatus comprising:
    a base panel;
    at least one height adjustment member, attached to the base panel, having a portion protruding upwardly from the base panel, a height of the portion being variable;
    at least one angle adjustment member, configured for supporting a device thereon, pivotably attached to the at least one height adjustment member, and configured to rotate to different angles to maintain the device at a predetermined angle, the drop test apparatus configured to be withdrawn in a horizontal direction to have the device fall down at the predetermined angle, the at least one angle adjustment member comprising a support panel, a backrest panel perpendicularly extended from the support panel, and a mounting block protruding from a lower side of the support panel, a pivot mounting slot defined in the mounting block, a pivot hole defined in a top portion of the at least one height adjustment member corresponds to the pivot mounting slot, and a pivot mounting member extending into the pivot hole and the pivot mounting slot for pivotably attaching the at least one angle adjustment member to the at least one height adjustment member.

2. The drop test apparatus of claim 1, wherein the pivot mounting member comprises a pivot shaft, extending into the pivot hole and the pivot mounting slot, and a V-shaped head connected to the pivot shaft.

3. The drop test apparatus of claim 1, wherein the at least one height adjustment member comprises a threaded post and a mounting piece protruding from the threaded post, and the pivot hole is defined in the mounting piece.

4. The drop test apparatus of claim 3, wherein an upper threaded retainer and a lower threaded retainer are secured to the threaded post and abut opposite sides of the base panel.

5. The drop test apparatus of claim 1, wherein at least one longitudinal slot is defined in the base panel, the at least one height adjustment member is engaged in the at least one longitudinal slot with the portion protruding upwardly from the base panel, and the portion is at a desired height.

6. The drop test apparatus of claim 1, wherein the at least one angle adjustment member comprises a support panel and a side panel perpendicularly extending from the support panel, and the side panel is pivotably attached to the at least one height adjustment member.

7. The drop test apparatus of claim 6, wherein an angled slot is defined in the side panel, a pivot hole is defined in the at least one height adjustment member, and a pivot mounting member is inserted into the pivot hole and the angled slot for pivotably attaching the at least one angle adjustment member to the at least one height adjustment member.

8. A drop test apparatus configured to perform drop test to a device, the drop test apparatus comprising:
    a base panel;
    a first height adjustment member, attached to the base panel;
    a second height adjustment member, attached to the base panel, parallel to the first height adjustment member;
    a first angle adjustment member, pivotably attached to the first height adjustment member, configured to rotate to a predetermined angle; and
    a second angle adjustment member, pivotably attached to the second height adjustment member, configured to rotate to the predetermined angle to maintain the device at the predetermined angle with the first angle adjustment member, the drop test apparatus configured to be withdrawn in a horizontal direction to have the device fall down at the predetermined angle, a pair of parallel longitudinal slots defined in the base panel, and the first height adjustment member and the second height adjustment member inserted through the pair of parallel longitudinal slots and attached to the base panel at different predetermined heights.

9. The drop test apparatus of claim 8, wherein the first angle adjustment member comprises a support panel and a backrest panel perpendicularly extending from the support panel.

10. The drop test apparatus of claim 9, wherein the first angle adjustment member further comprises a mounting block protruding from a lower side of the support panel; a pivot mounting slot is defined in the mounting block; a pivot hole is defined in the first height adjustment member corresponding to the pivot mounting slot; and a pivot mounting member is extended into the pivot hole and the pivot mounting slot for pivotably attaching the first angle adjustment member to the first height adjustment member.

11. The drop test apparatus of claim 10, wherein the pivot mounting member comprises a pivot shaft, extending into the pivot hole and the pivot mounting slot, and a V-shaped head connected to the pivot shaft.

12. The drop test apparatus of claim 10, wherein the first height adjustment member comprises a threaded post and a mounting piece protruding from the threaded post, and the pivot hole is defined in the mounting piece.

13. The drop test apparatus of claim 12, wherein an upper threaded retainer and a lower threaded retainer are secured to the threaded post and abut opposite sides of the base panel.

14. The drop test apparatus of claim 8, wherein the second angle adjustment member comprises a support panel and a side panel perpendicularly extending from the support panel, and the side panel is pivotably attached to the second height adjustment member.

15. The drop test apparatus of claim 14, wherein an angled slot is defined in the side panel, a pivot hole is defined in the second height adjustment member, and a pivot mounting member is inserted into the pivot hole and the angled slot.

16. A drop test apparatus comprising:
    a base panel;
    at least one height adjustment member, attached to the base panel, having a portion protruding upwardly from the base panel, a height of the portion being variable;
    at least one angle adjustment member, configured for supporting a device thereon, pivotably attached to the at least one height adjustment member, and configured to rotate to different angles to maintain the device at a predetermined angle, the at least one angle adjustment member comprising a support panel and a side panel perpendicularly extending from the support panel, the side panel pivotably attached to the at least one height adjustment member, an angled slot defined in the side panel, a pivot hole defined in the at least one height adjustment member, and a pivot mounting member inserted into the pivot hole and the angled slot for pivotably attaching the at least one angle adjustment member to the at least one height adjustment member.

\* \* \* \* \*